Jan. 13, 1959 H. C. SWIM Plant Pat. 1,796
ROSE PLANT
Filed Feb. 26, 1958
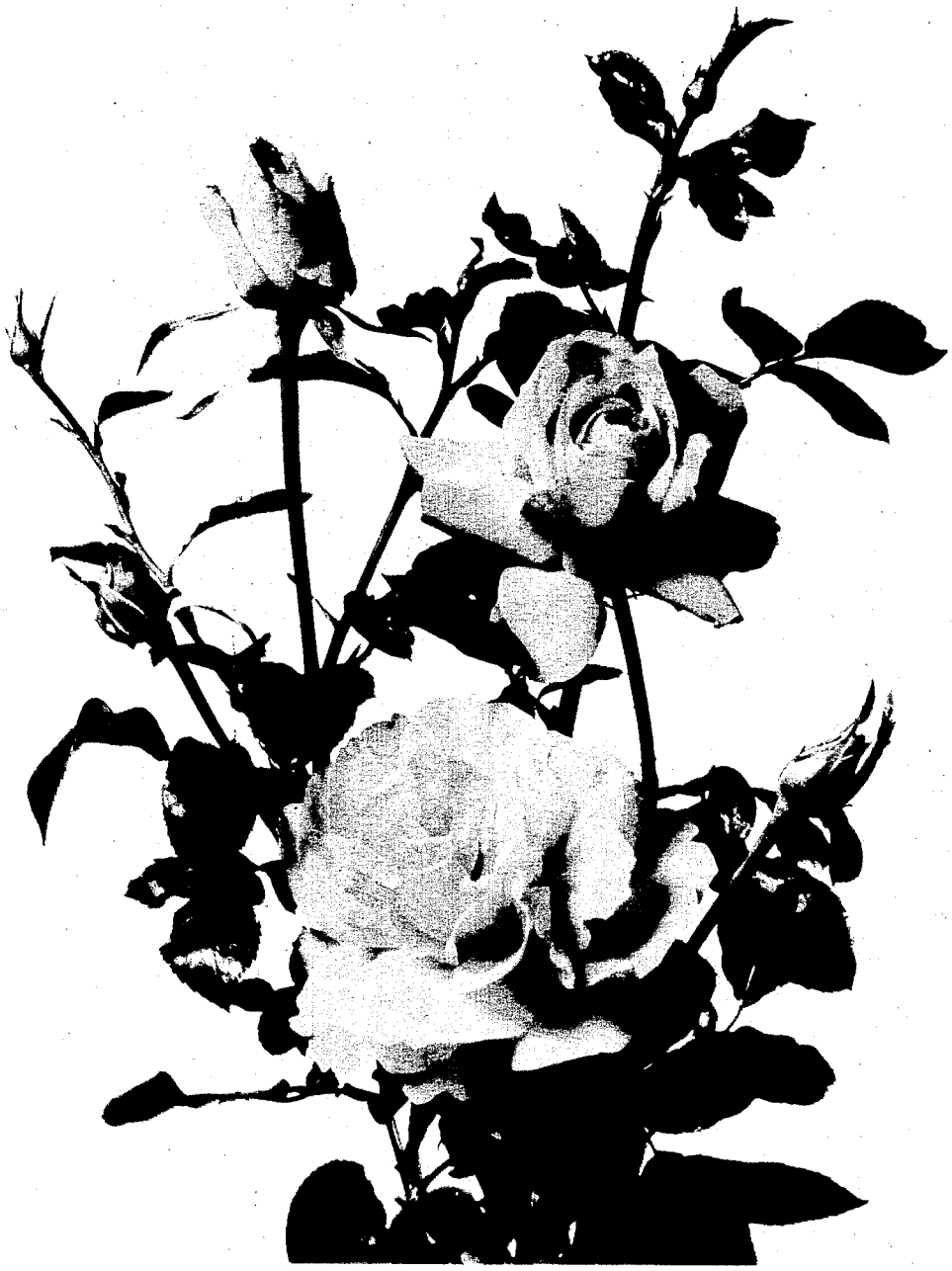
Inventor.
H. C. Swim
By: Robb & Robb
Attorneys.

United States Patent Office

Plant Pat. 1,796
Patented Jan. 13, 1959

1,796

ROSE PLANT

Herbert C. Swim, Ontario, Calif., assignor to Armstrong Nurseries, Inc., Ontario, Calif., a corporation of California Application February 26, 1958, Serial No. 717,794

1 Claim. (Cl. 47—61)

The present invention relates to a new and distinct variety of rose plant of the class falling between the hybrid tea and floribunda classes, which was originated by me by crossing the variety "Charlotte Armstrong" (Plant Patent No. 455) with the variety "Floradora" (unpatented).

The primary objective of this breeding was to produce a new variety which combines therein the most desirable characteristics of the two parents aforesaid. This objective was fully achieved, along with other improvements, as evidenced by the following unique combination of characteristics which are outstanding in the new variety:

(1) A very vigorous, much-branched and fast-breaking plant;

(2) Attractive, glossy, dark green foliage ranging in size from medium to large;

(3) A floriferousness which approaches that of the parent "Floradora";

(4) A habit of bearing flowers sometimes singly, sometimes in small clusters, and on stems of medium length;

(5) An attractive bud form, ranging from ovoid to urn-shaped, which opens to a well-formed, high-centered double flower, having from 25 to 35 petals;

(6) A flower size falling between that of "Charlotte Armstrong" and "Floradora";

(7) Better-than-average petal substance, approaching that of "Floradora," with attendant long-lasting qualities of the flower; and (8) A distinctive general color tonality of the flowers ranging between Cherry and Rose Red.

In comparison with its seed parent, "Charlotte Armstrong," the new variety has foliage which is glossier than that of this parent; it is more floriferous; its flowers tend to be borne sometimes in small clusters as well as sometimes singly, and on stems of medium length, whereas the flowers of "Charlotte Armstrong" are usually borne singly and on longer stems; the flowers are somewhat smaller than those of this parent; and the flowers are a darker red color than those of "Charlotte Armstrong."

As compared with its pollen parent, "Floradora," the new variety bears larger and better shaped flowers, which are red as distinguished from those of "Floradora" which are Scarlet-Orange in color.

From the foregoing, it will be recognized that the new variety is definitely differentiated from its parents, as well as from all other varieties of which I am aware, and asexual reproduction of the new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), except where general color terms of ordinary dictionary significance are obvious:

Type: Bush; greenhouse and outdoor; seedling; for cut flowers and for garden decoration.

Class: Between hybrid tea and floribunda.

Breeding: Seedling.

*Seed parent.*—"Charlotte Armstrong."

*Pollen parent.*—"Floradora."

Propagation: Holds its distinguishing characteristics through succeeding propagations by budding.

*Flower*

Locality where grown and observed: Ontario, California.

Flowers borne: Sometimes singly and sometimes from 3 to 5 or more to stem; on stems of normal strength and from medium length to long.

Quantity of bloom: Very abundant, both outdoors and in greenhouse.

Continuity: Nearly continuous during growing season.

Fragrance: Slight.

Bud:

*Peduncle.*—From average length to long; from slender to average caliper; erect; moderately smooth; some stipitate glands; occasional small prickles. Color—near Buffy Brown, Plate XL (Ridgway), overlaid with near Vandyke Red, Plate XIII (Ridgway) on side exposed to the sun.

*Before calyx breaks.*—Size—medium. Form—medium length; ovoid; with foliaceous appendages on the surface of the bud; usually with slender, much-cut foliaceous parts extending beyond the tip of the bud equal to ¼ or more of its length.

*As calyx breaks.*—Color—between Chrysanthemum Crimson, Plate 824/1, page 169 (Wilson) and Indian Lake, Plate 826/1, page 170 (Wilson).

*Sepals.*—Inner surface—with fine, woolly tomentum, and with margins of alternate sepals lined with fine, woolly tomentum; others lined with stipitate glands. Outer surface—moderately smooth.

*As first petal opens.*—Size—average. Form—medium length; from ovoid to urn-shaped. Color: outside—near Cardinal Red, Plate 822/1, page 168 (Wilson), with small area at base of petal near point of attachment near Uranium Green, Plate 63/2, page 63 (Wilson); inside—near Currant Red, Plate 821/1, page 167 (Wilson), with small area at base of petal near point of attachment near Uranium Green, Plate 63/2, page 63 (Wilson).

*Opening.*—Opens up well; is not retarded from opening by cold, hot, wet or dry weather.

Bloom:

*Size (when fully open).*—From average to large; from 3½ inches to 4½ inches.

*Petalage.*—Double; from 25 to 35 petals, plus from 4 to 6 petaloids; arranged regularly.

*Form.*—High-centered and somewhat globular at first, but becoming from cupped to high-centered; petals being at first somewhat loosely cupped, with lateral margins of outer petals usually reflexed ½ of petal length, and with apex of outer petals sometimes reflexed from ¼ to ½ of petal length, becoming later at maturity somewhat more loosely cupped, with lateral margins of intermediate and outer petals usually reflexed ⅔ or more of petal length, and with apex sometimes reflexed ½ or more of petal length.

Petals:

*Texture.*—Thick; leathery. Inside—from satiny to velvety. Outside—from shiny to satiny.

*Shape.*—Outer—broadly obovate, with apex flat and sometimes with 1 or 2 notches. Intermediate—broadly obovate, with apex from rounded to flat and with 1 or 2 notches. Inner—obovate and with a somewhat irregular margin; apex rounded, and with 1 or 2 notches.

This description of a newly opened flower was made from a rose grown outdoors in the month of October at Ontario, California:

*Color.*—Outer petal: outside surface—near Rose Red, Plate 724/1, page 158 (Wilson), with small area at base of petal near point of attachment between Uranium Green, Plate 63/2, page 63 (Wilson) and Uranium Green, Plate 63/3, page 63 (Wilson); inside surface—near Rose Red, Plate 724, page 158 (Wilson), with small area at base of petal near point of attachment between Uranium Green, Plate 63/2, page 63 (Wilson) and Uranium Green, Plate 63/3, page 63 (Wilson). Intermediate petal: outside surface—near Rose Red, Plate 724/3, page 158 (Wilson), with small area at base of petal near point of attachment between Uranium Green, Plate 63/2, page 63 (Wilson) and Uranium Green, Plate 63/3, page 63 (Wilson); inside surface—between Rose Red, Plate 724/1, page 158 (Wilson), and Rose Red, Plate 724, page 158 (Wilson), with small area at base of petal near point of attachment between Uranium Green, Plate 63/2, page 63 (Wilson) and Uranium Green, Plate 63/3, page 63 (Wilson). Inner petal: outside surface—between Cherry, Plate 722/1, page 157 (Wilson) and Cherry, Plate 722/2, page 157 (Wilson), with small area at base of petal near point of attachment between Uranium Green, Plate 63/2, page 63 (Wilson) and Uranium Green, Plate 63/3, page 63 (Wilson); inside surface—near Cherry, Plate 722, page 157 (Wilson), with small area at base of petal near point of attachment between Uranium Green, Plate 63/2, page 63 (Wilson) and Uranium Green, Plate 63/3, page 63 (Wilson).

This description was made from a rose that was open for 3 days outdoors in the month of October at Ontario, California:

*Color.*—Outer petal: outside surface—near Rose Red, Plate 724/1, page 158 (Wilson), with small area at base of petal near point of attachment near Uranium Green, Plate 63/3, page 63 (Wilson); inside surface—near Rose Red, Plate 724, page 158 (Wilson), with small area at base of petal near point of attachment near Uranium Green, Plate 63/3, page 63 (Wilson). Inner petal: outside surface—near Rose Red, Plate 724/1, page 158 (Wilson), with small area at base of petal near point of attachment near Uranium Green, Plate 63/3, page 63 (Wilson); inside surface—near Rose Red, Plate 724, page 158 (Wilson), with small area at base of petal near point of attachment near Uranium Green, Plate 63/3, page 63 (Wilson).

*General color effect.*—Newly opened flower—between Cherry, Plate 722/1, page 157 (Wilson) and Rose Red, Plate 724/1, page 158 (Wilson). 3-days open—between Cherry, Plate 722/2, page 157 (Wilson) and Cherry, Plate 722/1, page 157 (Wilson).

*Behavior.*—Drop off cleanly; not particularly affected by cold, hot, wet or dry weather.

*Flower longevity.*—On bush in garden—4 or 5 days in November. Cut roses grown outdoors and kept at living-room temperatures—5 or 6 days in November.

*Reproductive organs*

Stamens: Average number; arranged regularly about pistils; a few mixed with petaloids.

Filaments: From medium length to long; from 5 to 12 mm. in length; few without anthers. Color—near Carrot Red, Plate 612/1, page 71 (Wilson).

Anthers: From medium size to large; all open approximately at once. Color: upper side—margins near Indian Yellow, Plate 6/2, page 6 (Wilson), with remainder near Buttercup Yellow, Plate 5/3, page 5 (Wilson); under side—margins near Indian Yellow, Plate 6/2, page 6 (Wilson), with remainder near Buttercup Yellow, Plate 5/3, page 5 (Wilson).

Pollen: Moderate quantity. Color—near Lemon Yellow, Plate 4/2, page 4 (Wilson).

Pistils: Average number; approximately 75 in number.

Styles: Moderately even; average length; from 4 to 10 mm. in length; average caliper; bunched. Color—upper half near Carmine, Plate 21, page 21 (Wilson), with remainder near Sap Green, Plate 62/2, page 62 (Wilson).

Stigma: Color—near Egyptian Buff, Plate 407/1, page 122 (Wilson).

Ovaries: Usually all enclosed in calyx, but some protruding from calyx.

Hips: Short; globular; smooth; walls thick and fleshy. Color (near maturity)—near Orange, Plate III (Ridgway) on side exposed to the sun.

Sepals: Permanent; medium length; curled; re-curved. Color: inside—near Light Grape Green, Plate XLI (Ridgway); outside—near Chromium Green, Plate XXXII (Ridgway).

Seeds: Very few; usually from 1 to 5 in number per open-pollinated hip; medium size.

*Plant*

Foliage:

*Leaves.*—Compound of usually 3 to 7 leaflets; from normal abundance to abundant; from medium size to large; somewhat leathery; glossy.

*Leaflets.*—Shape—ovoid, with apex from obtuse to acute. Base—round. Margin—simply serrate.

*Color.*—Mature: upper surface—near Deep Dull Yellow-Green (2), Plate XXXII (Ridgway); under surface—near Light Elm Green, Plate XVII (Ridgway). Young: upper surface—near Dark Dull Yellow-Green, Plate XXXII (Ridgway); under surface—near Deep Corinthian Red, Plate XXVII (Ridgway).

*Rachis (the supporting stem of the compound leaf).*—Average size. Upper side—grooved; with some stipitate glands on edges. Under side—smooth; with few stipitate glands and 1 or 2 prickles.

*Stipules.*—From short to medium length; medium width; with short to medium length points turning out at an angle of more than 45°.

*Disease resistance.*—Better-than-average resistance to mildew, as compared with other varieties grown under comparable cultural conditions at Ontario, California.

Growth:

*Habit.*—Bushy; upright; much-branched.

*Growth.*—Very vigorous.

*Canes.*—Medium caliper.

*Main stems.*—Color—near Biscay Green, Plate XVII (Ridgway). Large prickles—several; medium length; straight; with long, narrow base; color—near Rood's Brown, Plate XXVIII (Ridgway). Small prickles—very few; color—near Rood's Brown, Plate XXVIII (Ridgway). Hairs—none.

*Branches.*—Color—near Deep Dull Yellow-Green (2), Plate XXXII (Ridgway). Large prickles—several; medium length; straight; with long, narrow base; color—near Sayal Brown, Plate XXIX (Ridgway). Small prickles—very few; color—near Sayal Brown, Plate XXIX (Ridgway). Hairs—none.

*New shoots.*—Color—near Courge Green, Plate XVII (Ridgway), overlaid with near Prussian Red, Plate XXVII (Ridgway). Large prickles—very few; short; almost straight; with narrow base of medium length; color—near Mineral Red, Plate XXVII (Ridgway). Small prickles — none. Hairs—none.

I claim:

A new and distinct variety of rose plant of the class between the hybrid tea and floribunda classes, substantially as herein shown and described, characterized particularly as to novelty by its unique combination of very vigorous, much-branched and fast-breaking habits of growth, attractive glossy dark green foliage of from medium to large size, a floriferousness approaching that of "Floradora" (unpatented), a habit of bearing flowers sometimes singly and sometimes in small clusters on stems of medium length, attractive buds ranging in form from ovoid to urn-shaped, well-formed, high-centered double flowers when fully open, a flower size between that of "Charlotte Armstrong" (Plant Patent No. 455) and "Floradora," better-than-average petal substance approaching that of "Floradora," with attendant long-lasting flower qualities, and a distinctive general color tonality of the flowers ranging between Cherry and Rose Red.

No references cited.